(12) United States Patent
Lubich et al.

(10) Patent No.: US 8,216,793 B2
(45) Date of Patent: Jul. 10, 2012

(54) DETECTION OF ANTIBODY THAT BINDS TO WATER SOLUBLE POLYMER-MODIFIED POLYPEPTIDES

(75) Inventors: Christian Lubich, Vienna (AT); Juergen Siekmann, Vienna (AT); Birgit Maria Reipert, Deutsch Wagram (AT); Hans-Peter Schwarz, Vienna (AT); Hartmut Ehrlich, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 12/786,641

(22) Filed: May 25, 2010

(65) Prior Publication Data

US 2011/0070592 A1 Mar. 24, 2011

Related U.S. Application Data

(60) Provisional application No. 61/181,191, filed on May 26, 2009.

(51) Int. Cl.
*G01N 33/566* (2006.01)
(52) U.S. Cl. .................. 435/7.1; 436/501; 436/518
(58) Field of Classification Search .................. None
See application file for complete search history.

(56) References Cited

U.S. PATENT DOCUMENTS

| | | | |
|---|---|---|---|
| 4,356,170 A | 10/1982 | Jennings et al. | |
| 7,683,158 B2 | 3/2010 | Siekmann et al. | |
| 2003/0143596 A1* | 7/2003 | Bentley et al. | 435/6 |
| 2005/0250678 A1* | 11/2005 | DeFrees et al. | 514/8 |
| 2007/0191597 A1 | 8/2007 | Jain et al. | |
| 2007/0244301 A1* | 10/2007 | Siekmann et al. | 530/383 |
| 2007/0282096 A1 | 12/2007 | Jain et al. | |

FOREIGN PATENT DOCUMENTS

WO WO-2008/063663 A2 5/2008

OTHER PUBLICATIONS

Lubich, Dissertation, "Anti-PEG antibodies in experimental animal disease models and in patients treated with PEGylated proteins," pp. 1-89, The University of Vienna, Austria (Aug. 1, 2008), available online Sep. 2, 2008, http://othes.univie.ac.at/1133/1/2008-09-02_0101340.pdf.*
Armstrong et al., "Occurrence of an Antibody to Poly(Ethylene Glycol) in Normal Donors", Blood, 102:556 A, Abstract 2042 (2003).
Armstrong et al., "Rapid Clearance of PEG-Asparaginase in ALL Patients by an Antibody Against Poly (Ethylene Glycol)", Blood (ASH annual Meeting Abstracts), 108:1856 A (2006).
Fernandes and Gregoriadis, "Polysialylated asparaginase: preparation, activity and pharmacokinetics", Biochim. Biophys. Acta., 1341:26-34 (1997).
Fisher et al., "Isolation and Identification of a Human Antibody to Poly (Ethylene Glycol)", Blood, 102(11):559 A, Abstract 2052 (2003).
Garratty, "Progress in modulating the RBC membrane to produce transfusable universal/stealth donor RBCs", Transfusion Medicine Reviews, 18(4):245-256 (2004).
Gregoriadis et al., "Improving the therapeutic efficacy of peptides and proteins: A role for polysialic acids", Int. J. Pharm., 300:125-130 (2005).
Halligan and Nair, "A highly efficient procedure for the oxidation of the 5'-position of adenosine analogues", ARKIVOC (ii), 101-106 (2006).
Harris and Chess, "Effect on pegylation on pharmaceuticals", Nat Rev Drug Discov., 2:214-221 (2003).
Hobbs and Heathrock, "A Second-Generation Synthesis of the C1-C28 Portion of the Altohyrtins (Spongistatins)", J. Am Chem. Soc., 125:12836-12843 (2003).
Kozlowski et al., "Development of Pegylated Interferons for the Treatment of Chronic Hepatitis C", BioDrugs, 5:419-29 (2001).
Roberts et al., "Chemistry for peptide and protein PEGylation", Advanced Drug Delivery Reviews, 54:459-476 (2002).
Schott et al., "Preparation, Characterization, and in vivo Biodistribution Properties of Synthetically Cross-linked Multivalent Antitumor Antibody Fragments", Bioconjugate Chem., 4:153-165 (1993).
Veronese, "Branched and Linear Poly(Ethylene Glycol): Influence of the Polymer Structure on Enzymological, Pharmacokinetic, and Immunological Properties of Protein Conjugates", Bioact. Compat. Polym., 12:196-207 (1997).
Veronese et al., "Introduction and overview of peptide and protein pegylation", in Harris, Advan. Drug Deliv. Rev., 54:453-456 (2002).
Yamasaki,"Novel Polyethylene Glycol Derivatives for Modification of Proteins", Agric. Biol. Chem., 52:2125-2127 (1988).
International Search Report or PCT/US2010/036011 dated Aug. 6, 2010.
Written Opinion for PCT/US2010/03601 dated Aug. 6, 2010.

* cited by examiner

*Primary Examiner* — Shafiqul Haq
*Assistant Examiner* — Galina Yakovleva
(74) *Attorney, Agent, or Firm* — Marshall, Gerstein & Borun LLP

(57) ABSTRACT

The present invention provides analytical methods for detecting anti-polymer antibody in an individual. The methods involve contacting a sample from the individual with a water soluble polymer-modified carrier and detecting binding of antibody to the water soluble polymer on the water soluble polymer-modified carrier wherein binding is indicative of the presence of antibody to the water polymer-modified polypeptide. Antibody may be detected to water soluble polymers such as polyethylene glycol, polysialic acid, dextran, hydroxyalkyl starch, or hydroxyethyl starch. When antibody to the water soluble polymer polyethylene glycol is to be detected, the carrier is modified with a non-linear polyethylene glycol derivative.

13 Claims, 12 Drawing Sheets

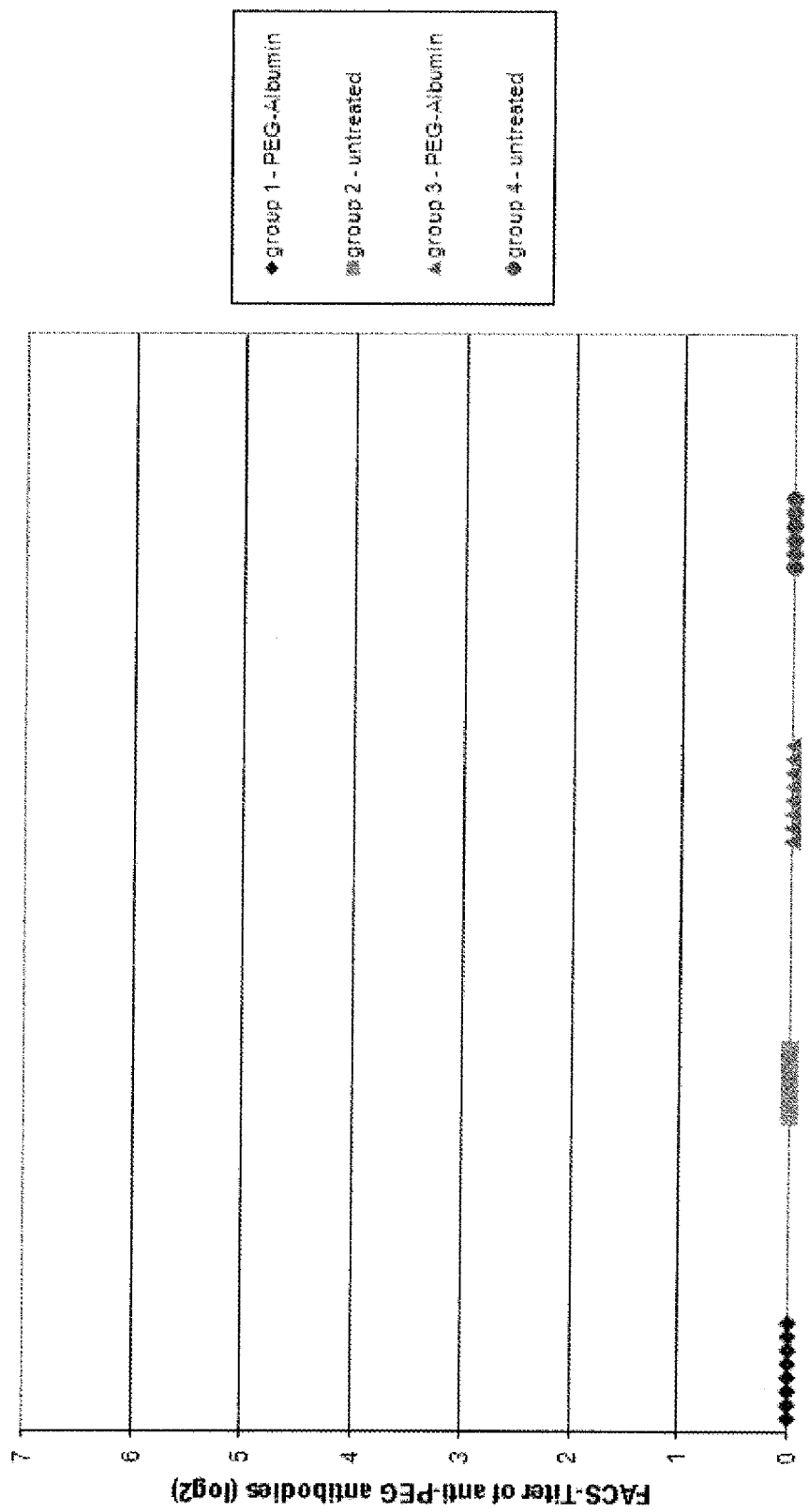
Figure 7.1

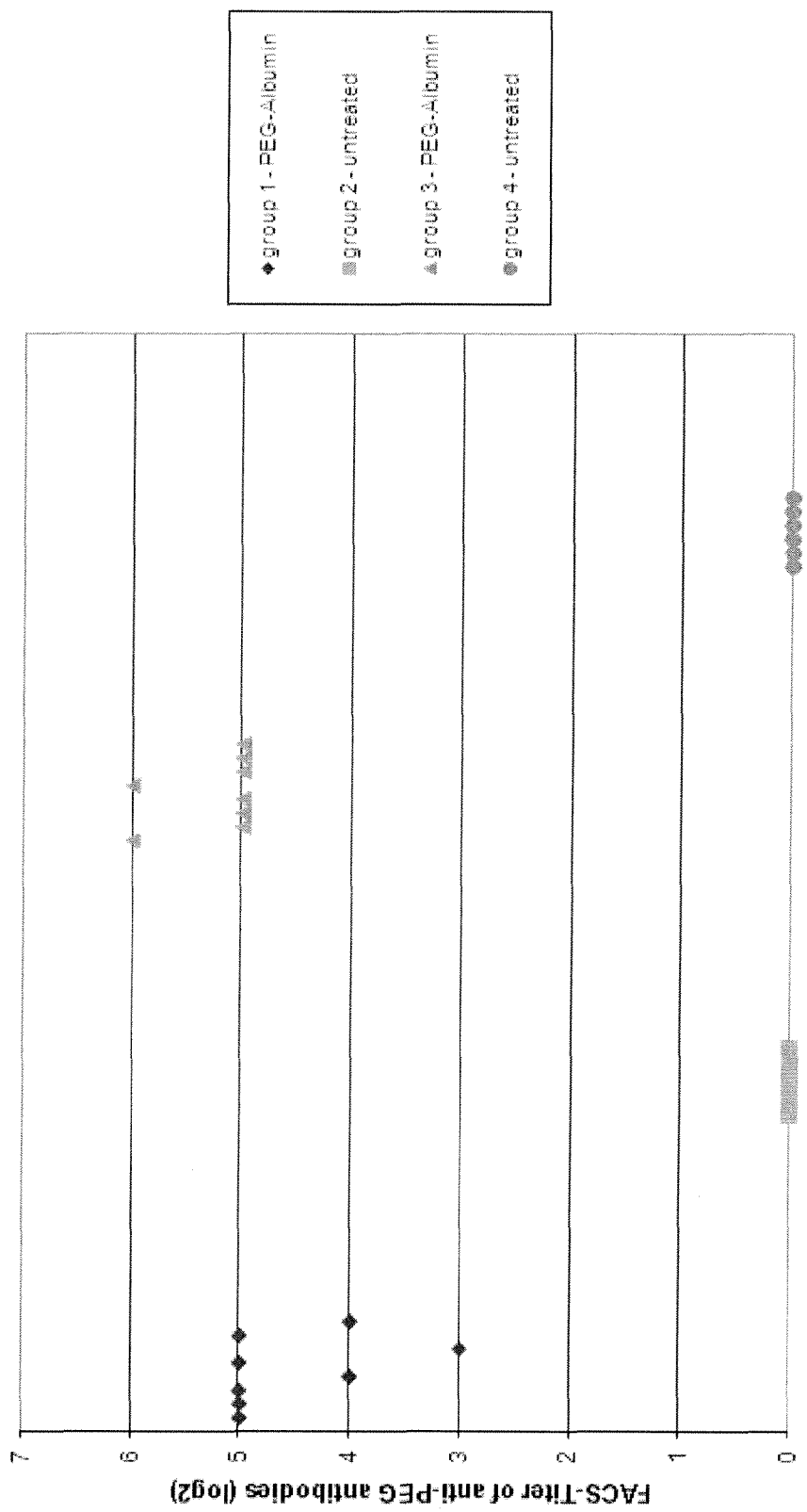
Figure 7.2

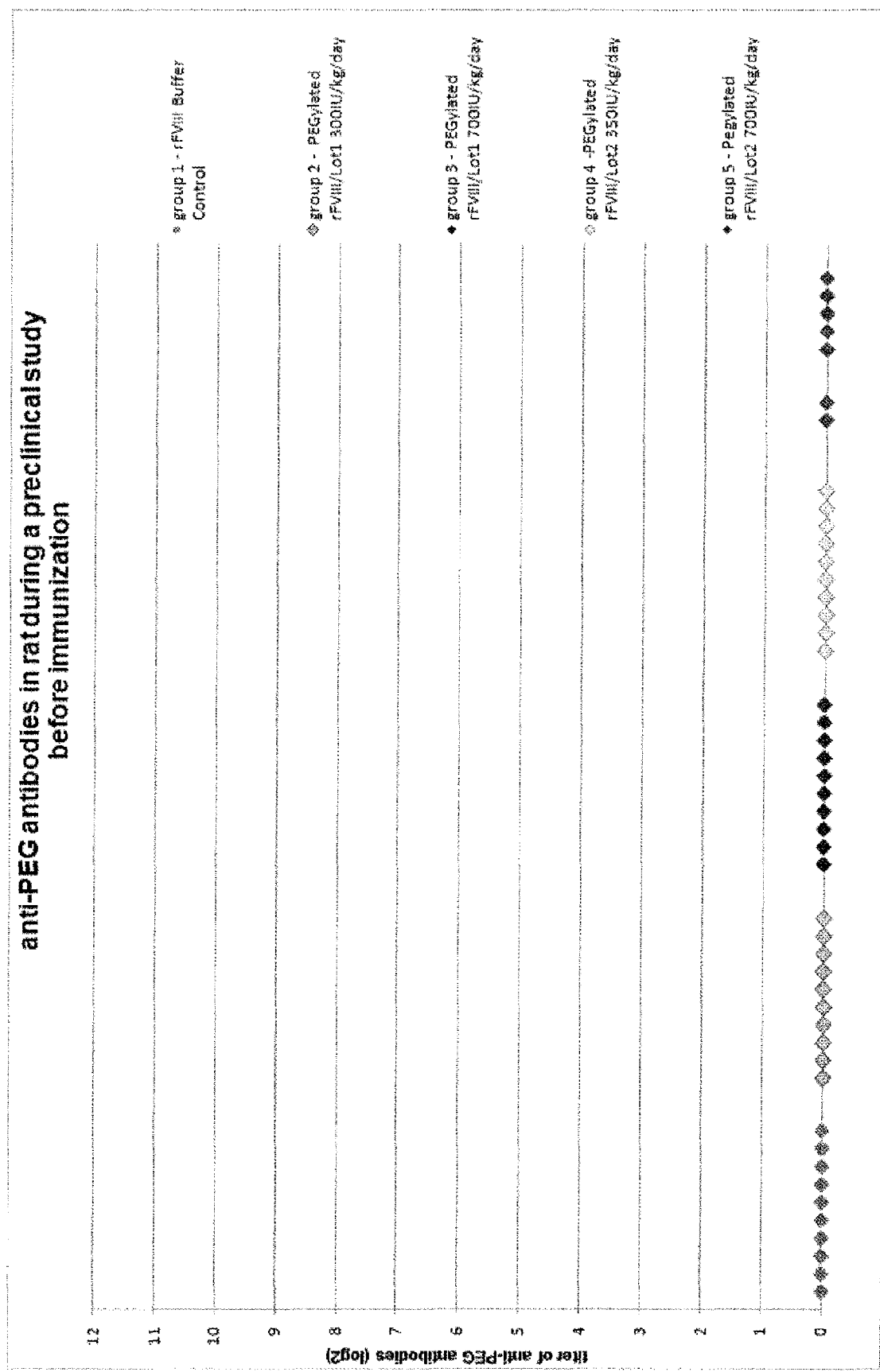
Figure 8.1

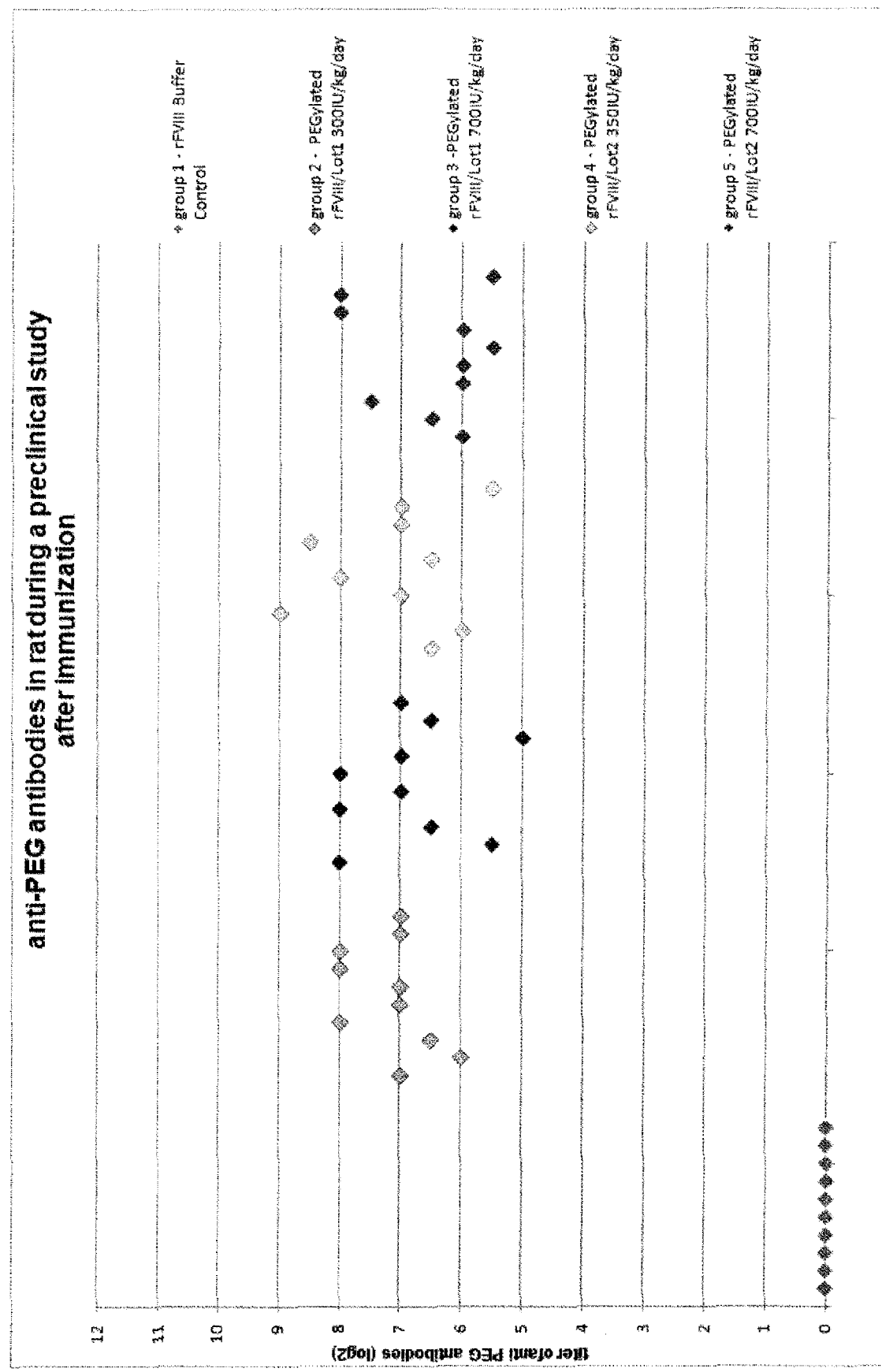
Figure 8.2

DETECTION OF ANTIBODY THAT BINDS TO WATER SOLUBLE POLYMER-MODIFIED POLYPEPTIDES

This application claims priority from U.S. Provisional Patent Application No. 61/181,191, filed May 26, 2009, which is incorporated by reference herein.

FIELD OF THE INVENTION

The present invention provides analytical methods for detecting anti-polymer antibody in an individual. The methods involve contacting a sample from the individual with a water soluble polymer-modified carrier and detecting binding of antibody to the water soluble polymer on the water soluble polymer-modified carrier. Binding is indicative of the presence of antibody to the water polymer-modified polypeptide. Antibody may be detected to water soluble polymers such as polyethylene glycol, polysialic acid, dextran, hydroxyalkyl starch, or hydroxyethyl starch. When antibody to the water soluble polymer polyethylene glycol is to be detected, the carrier is modified with a non-linear polyethylene glycol derivative.

BACKGROUND OF THE INVENTION

In the body, polypeptide drugs are rapidly degraded by proteolytic enzymes and/or neutralized by antibodies. This reduces the half-life and circulation time of the drugs, limiting their therapeutic effectiveness. Attempts to address these limitations have included manipulation of the amino acid sequence of the polypeptide to decrease immunogenicity and proteolytic cleavage, fusion or conjugation of the polypeptide to immunglobulins and serum proteins, incorporation of the polypeptide into drug delivery vehicles for protection and slow release, and conjugation of the polypeptide to natural or synthetic polymers. See, Roberts et al., *Advanced Drug Delivery Reviews*, 54: 459-476 (2002).

Addition of water soluble polymers or carbohydrates to polypeptide drugs has been shown to prevent their degradation and increase their half-life. For instance, "PEGylation" of polypeptide drugs protects them and improves their pharmacodynamic and pharmacokinetic profiles. See, Harris and Chess, *Nat Rev Drug Discov*, 2:214-221 (2003). The PEGylation process attaches repeating units of polyethylene glycol (PEG) to a polypeptide drug. PEGylation of molecules can lead to increased resistance of drugs to enzymatic degradation, increased half-life in vivo, reduced dosing frequency, decreased immunogenicity, increased physical and thermal stability, increased solubility, increased liquid stability, and reduced aggregation. Examples of polypeptide drugs conjugated with PEG are PEG-asparaginase, PEG-interferons, PEG-filgrastim and PEG-adenosine deaminase.

PEG is a hydrophilic, uncharged, inert, biocompatible synthetic polymer. In its most common form, PEG is a linear or branched polyether terminated with hydroxyl groups and having the general structure:

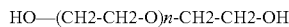

HO—(CH2-CH2-O)n-CH2-CH2-OH

PEG is synthesized by anionic ring opening polymerization of ethylene oxide starting with a nucleophilic attack of a hydroxide ion on the expoxide ring. An important aspect of PEGylation is the incorporation of various PEG functional groups that are used to attach the PEG to the peptide or protein. Most useful for polypeptide modification is monomethoxy PEG, mPEG, having the general structure:

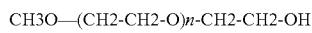

CH3O—(CH2-CH2-O)n-CH2-CH2-OH

Compared with other polymers, PEG has a relatively narrow polydispersity in the range of 1.01 for low molecular weight PEGs (<5 kDa) to 1.1 for high molecular weight PEGs (>50 kDa). Polydispersity is calculated by dividing the weight average molecular weight with the number average molecular weight, and indicates the distribution of individual molecular masses in a batch of polymers (Roberts et al., supra). PEG is soluble in both aqueous and organic solutions, which makes it suitable for end group derivatization and chemical conjugation to biological molecules under mild physiological conditions.

For the coupling reaction between the PEG and the molecule of interest, it is necessary to activate PEG by making a derivative of the PEG having a functional group at one or both termini. The choice of which functional group to activate is depends on the reactive groups on the molecule that will be coupled.

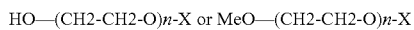

HO—(CH2-CH2-O)n-X or MeO—(CH2-CH2-O)n-X

X: functional group for coupling to protein

The most common route for PEG conjugation of proteins has been to activate the PEG with functional groups suitable for reactions with lysine and N-terminal amino acid groups. The monofunctionality of methoxyPEG makes it particularly suitable for protein and peptide modification because it yields reactive PEGs that do not produce cross-linked polypeptides, as long as diol PEG has been removed (Roberts et al., supra).

Branched structures of PEG have also been proven to be useful for PEGylation of a protein or a peptide. For example, a branched PEG attached to a protein has properties of a much larger molecule than a corresponding linear mPEG of the same molecular weight. See, Yamasaki, *Agric. Biol. Chem.*, 52: 2125-2127 (1988). Branched PEGs also have the advantage of adding two PEG chains per attachment site on the protein, therefore reducing the chance of protein inactivation due to attachment. Furthermore, these structures are more effective in protecting proteins from proteolysis, in reducing antigenicity and in reducing immunogenicity. See, Veronese, *Bioact. Compat. Polym.*, 12: 196-207 (1997).

PEG has long been thought to be non-immunogenic. However, it was shown in recent reports that treatment with PEGylated drugs can lead to the development of anti-PEG antibodies in animal disease models and in patients. Those antibodies caused a rapid clearance of the PEGylated proteins from the circulation. Moreover, a considerable amount of anti-PEG antibody in healthy donors was reported in some studies.

To evaluate the incidence of anti-PEG antibodies within a normal, healthy human population, Armstrong et al. [Blood, 102: 556 A (2003)] analyzed 250 plasma samples of normal donors. Anti-PEG antibodies were detected using TentaGel® beads consisting of a PEG-engrafted polystrene matrix. Of the samples analyzed, 25.2% of samples were positive for IgG and/or IgM, of which 18.4% showed IgG binding only, 3.6% IgM only, and 3.2% both. A further study performed in acute lymphocytic leukemia subjects receiving PEG-asparaginase demonstrated the development of anti-PEG antibodies [Armstrong et al., Blood (ASH annual Meeting Abstracts), 108: 1856 A (2006)]. Nine of fifteen subjects who showed undetectable asparaginase activity tested positive by serology and thirteen tested positive when using the flow cytometry, whereas a cohort of thirteen subjects with normal sustained levels of asparaginase activity after treatment did not develop detectable anti-PEG antibodies. In approximately one third of the patients that developed anti-PEG antibodies, rapid clearance of PEG-asparaginase rendered treatment ineffective. No relationship was observed between the presence of anti-PEG antibodies and serum asparaginase activity for patients treated with unmodified asparaginase.

International Publication No. WO 2008/063663 describes assays for detecting anti-PEG antibody in a biological sample.

As alternative to PEGylation, the coupling of polysialic acid (PSA) to therapeutic proteins is used to improve the pharmacokinetic properties. See Fernandes and Gregoriadis, *Biochim. Biophys. Acta.*, 1341: 26-34 (1997) and Gregoriadis et al., *Int. J. Pharm.* 300:125-130 (2005). U.S. Publication No. 2007/0282096 describes conjugating an amine or hydrazide derivative of PSA to proteins.

Polysialic acid, also referred as colominic acid (CA), is a natural occurring polysaccharide. It is a homopolymer of N-acetylneuraminic acid with α(2→8) ketotsidic linkage and contains vicinal diol groups at its non-reducing end. It is negatively charged and is a natural constituent of the human body.

There remains a need in the art for methods to detect anti-polymer antibodies in individuals who may receive or are receiving water soluble polymer-modified drugs.

DETAILED DESCRIPTION

The present invention provides analytical methods for detecting anti-polymer antibodies in a biological sample (such as blood, plasma or serum) from an individual. Pre-screening and/or monitoring individuals for anti-polymer antibodies allows for design of dosing strategies for individuals for whom a polymer-modified drug is indicated. Pre-screening and/or monitoring individuals for anti-polymer antibodies may also identify individuals for whom a non-polymer-modified drug may be indicated.

The invention provides a first type of method of detecting antibodies to a water soluble polymer-modified polypeptide in a sample that involves contacting the sample with a water soluble polymer-modified carrier and detecting binding of antibody to the water soluble polymer on the water soluble polymer-modified carrier, wherein the water soluble polymer is a non-linear water soluble polymer and wherein binding is indicative of the presence of antibody to the water polymer-modified polypeptide.

The term polypeptide as used in this document includes any peptide, polypeptide or protein. In some embodiments, the polypeptide is a blood coagulation protein. Blood coagulation proteins contemplated include, but are not limited to, Factor VIII, von Willebrand factor, Factor IX and Factor VIIa. Thus, methods of the invention of the first type are used to detect antibody to the PEG moiety of PEGylated Factor VIII. They are also employed to detect antibody to the PEG moiety of PEGylated von Willebrand factor. Antibody to the PEG moiety of PEGylated Factor IX is also detected by the methods. The methods are also used to detect antibody to the PEG moiety of PEGylated Factor VIIa.

In some embodiments of this first type of method the non-linear water soluble polymer is a non-linear polyethylene glycol (PEG) derivative. The non-linear PEG derivative may, for example, be branched (a PEG reagent having a functional group and containing two PEG chains attached to a central core) or multi-armed (a PEG reagent having a functional group and containing more than two PEG chains attached to a central core). Numerous non-linear PEG reagents are readily available in the art.

Non-linear PEG derivatives contemplated include, but are not limited to, non-linear PEG derivatives having a glycerol backbone with a 1,2 or 1,3 substitution pattern or a lysine backbone. The structures of some non-linear PEG derivatives contemplated include, but are not limited to, one or more of the following.

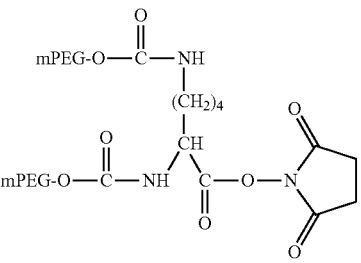

This structure of this branched reagent is based on a lysine backbone. The reagent is described in more detail by Kozlowski et al. [*BioDrugs*, 5: 419-29 (2001)].

2,3-Bis(methylpolyoxyethylene-oxy)-1-(1,5-dioxo-5-succinimidyloxy, pentyloxy)propane (NOF Corporation, Tokyo, Japan)

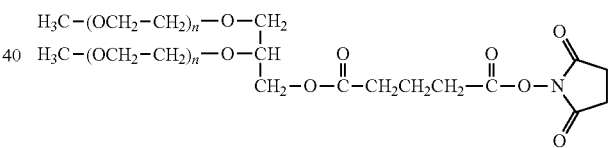

2,3-Bis(methylpolyoxyethylene-oxy)-1-(succinimidyl carboxypentyloxy)propane (NOF Corporporation, Tokyo, Japan)

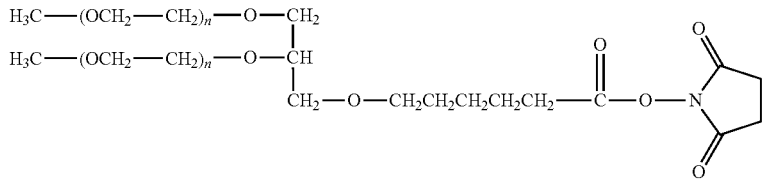

The two propane derivatives above have a glycerol backbone with a 1,2 substitution pattern. Branched PEG derivatives based on glycerol structures with 1,3 substitution or other branched structures described in US2003/0143596A1 can also be used.

In one embodiment, the branched PEG derivative is 1,3-Bis(methoxypoly(ethylene glycol)carbamoyl)-2-propanoxy-4-succinimidyl butanoate.

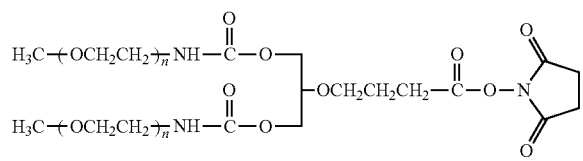

As noted, non-linear PEG derivatives contemplated include multi-armed derivatives. Thus, non-linear PEG derivatives contemplated also include, but are not limited to, a four-arm PEG such as the following.

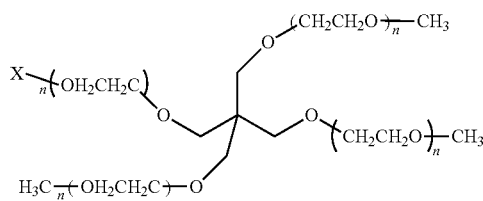

X: functional group

In another embodiment contemplated, the branched PEG derivative (Pierce, Rockford, Ill.) has three PEG branches, which are attached to a 4-unit PEG stem.

In yet another embodiment, the branched PEG derivative (JenKem Technology USA, Allen, Tex.) is a Y-shaped reagent with the structure:

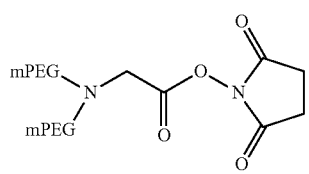

In the first type of method of the invention, the non-linear PEG derivative is either directly linked to the carrier or is linked to the carrier via a spacer molecule.

PEGylation chemistry is well known in the art. PEG and other water soluble polymers can be conjugated to carriers for use in methods of the invention by various different chemical reactions. Some PEG reagents contain NHS groups (see structures above) that react with primary amino groups. Other conjugation methods involve the coupling of water soluble polymers via aldehydes to amino groups by reductive animation or the coupling of a polymer having a maleamide (MAL) group to free sulfhydryl (SH) groups. Alternatively, the polymer could have a free amino group that can be coupled to a free carboxyl group via carbodiimide chemistry. A variety of publications describe coupling chemistry for PEGylation. See, for example, Roberts et al., *Advan. Drug Del. Rev.,* 54: 459-476 (2002) and Veronese et al. in Harris, *Advan. Drug Deliv. Rev.* 54: 453-456 (2002). In principal, any conjugation chemistry can be used for the conjugation of a water soluble polymer to a carrier for use in methods of the invention.

In some embodiments, the non-linear PEG derivative is directly linked to the carrier via an amide bond. In other embodiments, the non-linear PEG derivative is directly linked to the carrier via an amine group. The non-linear PEG derivative may also be directly linked to the carrier via other bonds resulting from PEGylation methods standard in the art.

In some embodiments, the non-linear PEG derivative is linked to the carrier via a spacer molecule wherein the spacer molecule itself is a PEG moiety.

In other embodiments, the spacer is a low molecular weight spacer with functional groups on each end. Examples of

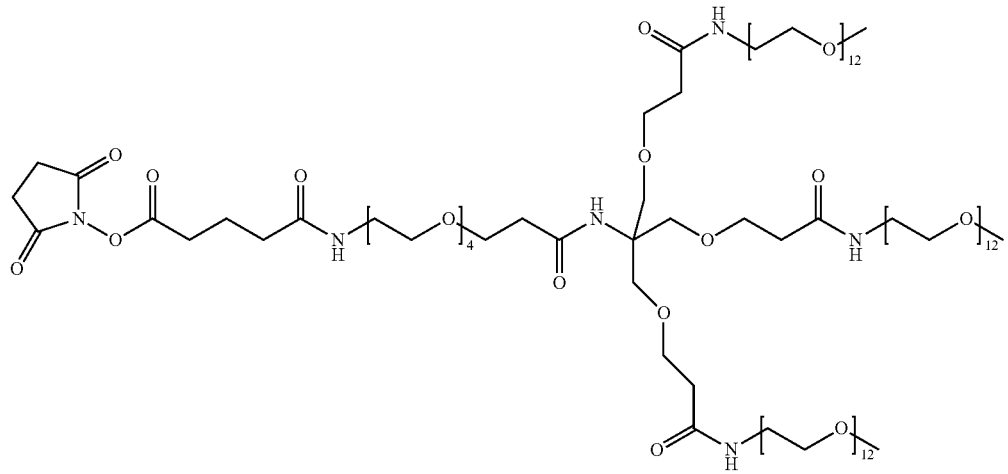

bifunctional spacers are the homobifunctional spacers DSS (Disuccinimidyl suberate) or the water soluble analog BS3 (Bis[Sulfosuccinimidyl]suberate) containing two active NHS groups for coupling to amino groups. Example of heterobifunctional spacers are EMCS (N-[ε-Maleimidocaproyloxy] succinimide ester) and the water soluble analog Sulfo-EMCS (N-[ε-Maleimidocaproyloxy]sulfosuccinimide ester as well as MBS (m-Maleimidobenzoyl-N-hydroxysuccinimide ester) and Sulfo-MBS (m-Maleimidobenzoyl-N-hydroxysulfosuccinimide ester), all having a reactive maleimido (MAL) group (for coupling to free SH-groups) and a NHS group (for coupling to amino groups). Other examples for heterobifunctional linker systems are Sulfo-KMUS (N-[κ-Maleimidoundecanoyloxy]-sulfosuccinimide ester) with a maleamide (MAL) and a NHS group and KMUA (N-κ-Maleimidoundecanoic acid) containing a MAL group and a free carboxyl group (for coupling to amino groups).

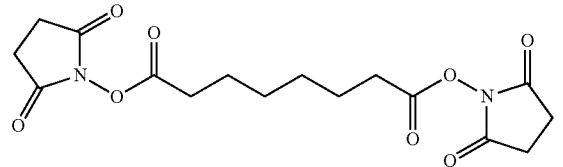

DSS

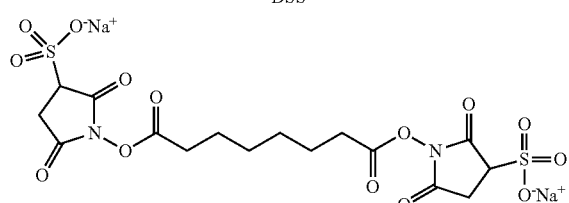

BS3

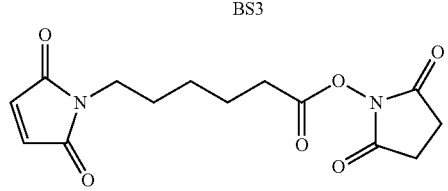

EMCS

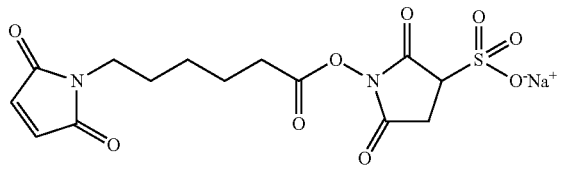

Sulfo-EMCS

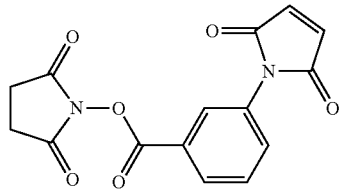

MBS

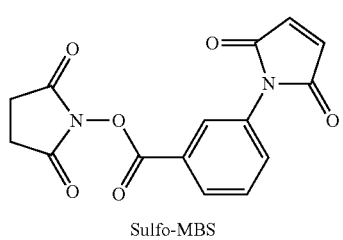

Sulfo-MBS

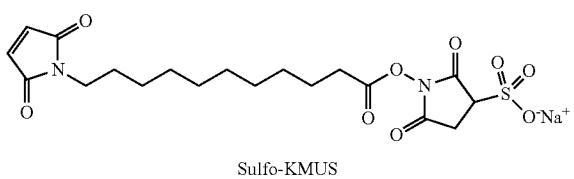

Sulfo-KMUS

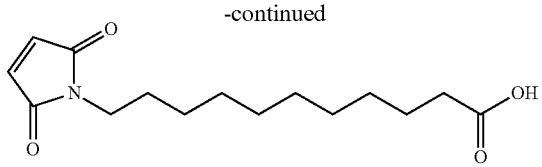

KMUA

Various spacers are available from, for example, Thermo Scientific Pierce Protein Research Products (Rockford, Ill.)

In another embodiment, the spacer is multifunctional. Examples of multifunctional linkers are MDSI and SDMB (Molecular Biosciences, Boulder, Colo.). These linker systems have two different reactive (NHS and MAL) groups and allow the formation of branched structures on the bead surface (see Example 15).

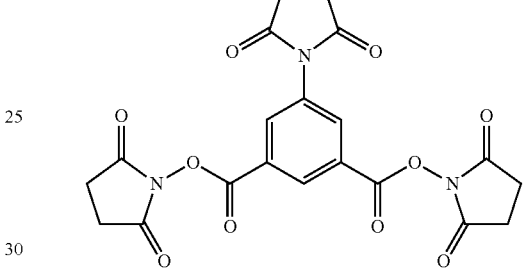

Maleimido-3,5-disuccinimidyl isophtalate (MDSI)

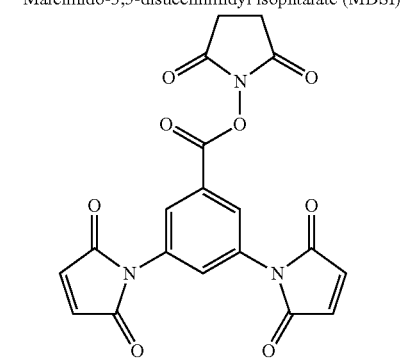

Succinimidyl-3,5-dimaleimidophenyl benzoate (SDMB)

The non-linear water soluble polymer of the first type of method is not limited to a PEG derivative. For example, the non-linear water soluble polymer may be a polysialic acid (PSA) moiety. In another embodiment, the non-linear water soluble polymer is dextran. In yet another embodiment, the non-linear water soluble polymer is hydroxyalkyl starch (HAS). In still a different embodiment, the non-linear water soluble polymer is hydroxyethyl starch (HES). In fact, the non-linear water soluble polymer may be any non-linear water soluble polymer with which a drug may be modified. For example, non-linear forms of poly(alkylene oxide), poly(vinyl pyrrolidone), poly(vinyl alcohol), polyoxazoline, and poly(acryloylmorpholine) are contemplated.

PSA is useful in methods of the invention when conjugated to carrier to detect antibodies to PSA-modified drugs. Sialic acid moieties are bound to carriers, for example, by the method described in U.S. Pat. No. 4,356,170 which is incorporated herein by reference. In addition, US Publication No. 2007/0191597 describes PSA derivatives containing an aldehyde group for reaction with substrates (e.g., proteins) at the reducing terminal end. Other techniques for coupling PSA are also known in the art.

Detection of binding in methods of the invention may be accomplished by any antibody/antigen binding detection technique known in the art such as flow-cytometry, Enzyme Linked Immunosorbent Assay (ELISA), radioimmunoassay (RIA), or immunoassay methods using magnetic beads. In methods of the invention, the water soluble polymer with which the carrier is modified is the "antigen." An appropriate carrier is chosen for use in the particular detection technique. For example, water soluble polymer may be conjugated to beads for use in flow cytometry. In some embodiments, the water soluble polymer-modified beads are polystyrene beads modified with a water soluble polymer. The water soluble polymer-modified polystyrene beads may be TentaGel® M $NH_2$ beads (grafted copolymers consisting of a low cross-linked polystyrene matrix on which a linear polyethylene glycol moiety is grafted) modified with a water soluble polymer. In other embodiments, the water soluble polymer-modified beads are silica beads modified with a water soluble polymer. The beads may also be latex or poly(methyl methacrylate) (PMMA) beads. In all the methods of the invention, the modified carriers may be modified with one, or more than one, type of water soluble polymer. Thus, the invention also provides water soluble polymer-modified carriers onto which water soluble polymer is grafted. For example, TentaGel M $NH_2$ beads modified with 1,3-Bis(methoxypoly(ethylene glycol)carbamoyl)-2-propanoxy-4-succinimidyl butanoate are provided.

Also contemplated are kits comprising non-linear water soluble polymer-modified carrier and a label describing use of the carrier according to a method of the invention of the first type described above. In some embodiments where the kits comprise non-linear water soluble polymer-modified carriers that are beads, the beads are lyophilized and the label additionally describes the reconstitution of the beads for use in the method.

The invention provides a second type of method of detecting antibodies to a water soluble polymer-modified polypeptide in a sample that involves contacting the sample with a water soluble polymer-modified carrier and detecting binding of antibody to the water soluble polymer on the water soluble polymer-modified carrier, wherein the water soluble polymer is not PEG or a derivative thereof and wherein binding is indicative of the presence of antibody to the water polymer-modified polypeptide.

In some embodiments of the second type of method, the polypeptide is a blood coagulation protein. Blood coagulation proteins contemplated include but are not limited to Factor VIII, von Willebrand factor, Factor IX and Factor VIIa. Thus, methods of the invention of the first type are used to detect antibody to the polymer moiety of water soluble polymer-modified Factor VIII. They are also employed to detect antibody to the polymer moiety of water soluble polymer-modified von Willebrand factor. Antibody to the polymer moiety of water soluble polymer-modified Factor IX is also detected by the methods. The methods are also used to detect antibody to the polymer moiety of water soluble polymer-modified Factor VIIa.

The water soluble polymer of the second type of method may be a linear or non-linear water soluble polymer. Water soluble polymers contemplated include, but are not limited to, PSA, dextran, HAS and HES. For example, the water soluble polymer may be a PSA moiety. In another embodiment, the water soluble polymer is dextran. In yet another embodiment, the water soluble polymer is HAS. In still a different embodiment, the water soluble polymer is HES. The water soluble polymer may be any water soluble polymer with which a carrier may be modified. For example, linear and non-linear forms of poly(alkylene oxide), poly(vinyl pyrrolidone), poly(vinyl alcohol), polyoxazoline, and poly(acryloylmorpholine) are contemplated.

As in the first type of method, detection of binding in the second type of method may be accomplished by any antibody/antigen binding detection technique known in the art such as flow-cytometry, Enzyme Linked Immunosorbent Assay (ELISA), radioimmunoassay (RIA), or immunoassay methods using magnetic beads. Also as in the first type of method, an appropriate carrier is chosen for use in the particular detection technique. For example, water soluble polymer may be conjugated to beads for use in flow cytometry. In some embodiments, the water soluble polymer-modified beads are polystyrene beads modified with water soluble polymer. The water soluble polymer-modified polystyrene beads may be TentaGel® M $NH_2$ beads (grafted copolymers consisting of a low cross-linked polystyrene matrix on which a linear polyethylene glycol moiety is grafted) modified with a water soluble polymer. In other embodiments, the water soluble polymer-modified beads are silica beads modified with a water soluble polymer. The beads may also be latex or poly(methyl methacrylate) (PMMA) beads. In all the methods of the invention, the modified carriers may be modified with one or more than one type of water soluble polymer. Thus, the invention provides water soluble polymer-modified carriers onto which water soluble polymer is grafted.

Also contemplated are kits comprising water soluble polymer-modified carrier and a label describing use of the carrier according to a method of the invention of the second type. In some embodiments where the kits comprise water soluble polymer-modified carriers that are beads, the beads are lyophilized and the label additionally describes the reconstitution of the beads for use in the method.

In embodiments of the invention, methods may be used to detect anti-polymer antibodies in individuals who are candidates to receive or who are receiving polypeptide drugs modified with water soluble polymers. Modified polypeptides contemplated, include, but are not limited to, modified versions of asparaginase, interferons, filgrastim, adenosine deaminase, Factor VIII, von Willebrand factor, Factor IX and Factor VIIa. The methods may also be used to detect antibody to water soluble polymer-modified red blood cells.

FIGURES

FIG. 1 shows an overview of the experimental set up of the anti-PEG detection assay.

FIG. 2 shows the verification that the detected antibodies are directed against PEG by using a competition assay. A monoclonal anti-PEG antibody was pre-incubated with a soluble PEG (wt=200) in different dilutions, before they were mixed together with the TentaGel® beads (grafted copolymers consisting of a low cross-linked polystyrene matrix on which a linear polyethylene glycol moiety is grafted).

FIG. 3 shows a comparison of TentaGel® beads (grafted copolymers consisting of a low cross-linked polystyrene matrix on which a linear polyethylene glycol moiety is grafted) with and without additional PEGylation, using mice plasma samples. The mice were treated intravenously with PEGylated protein. The results indicate a higher sensitivity of the anti-PEG detection assay when using TentaGel® beads that were additionally PEGylated with a branched PEG.

FIG. 4 shows a representative analysis of auto fluorescence comparing TentaGel® beads (grafted copolymers consisting of a low cross-linked polystyrene matrix on which a linear polyethylene glycol moiety is grafted) with and without additional PEGylation.

FIG. 5 shows the stability of the lyophilized TentaGel® beads (grafted copolymers consisting of a low cross-linked polystyrene matrix on which a linear polyethylene glycol moiety is grafted) with additional PEGylation. Different batches of TentaGel® beads with additional PEGylation were compared; all batches were stored for 4 weeks under 3 different conditions, 4° C., room temperature and 37° C. The beads were tested with a protein A purified anti-PEG antibody from rabbit, before and after storage.

FIG. 7 shows the evidence of anti-PEG antibodies in rats before treatment with PEG-Albumin (FIG. 7.1) and after treatment with PEG-Albumin of group 1 and 3 (FIG. 7.2.).

FIG. 8 shows evidence of anti-PEG antibodies in rats before treatment with PEGylated Factor VIII (FIG. 8.1) and after treatment with different concentrations and lots (FIG. 8.2.)

EXAMPLES

Figure 1:
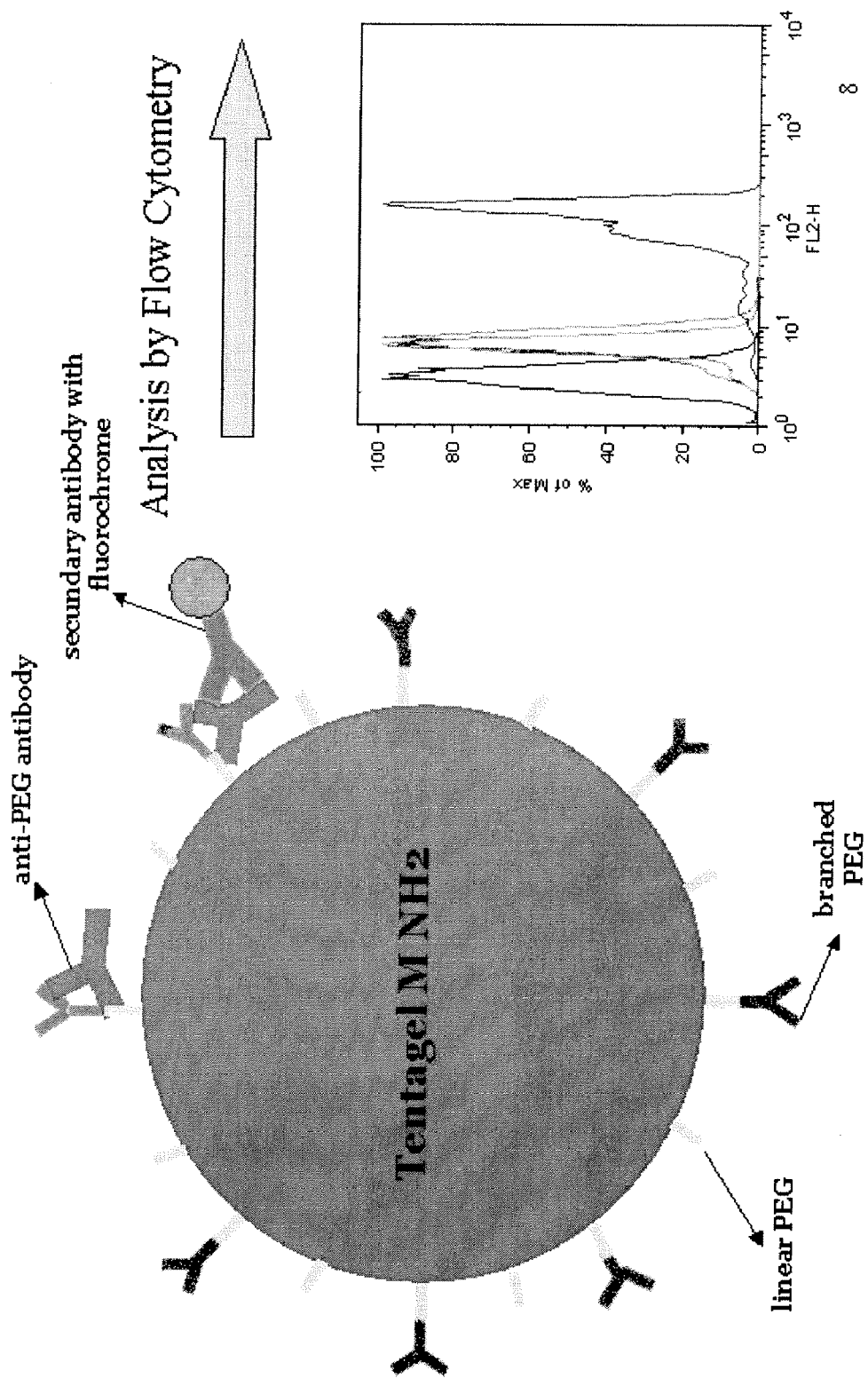

The present invention is illustrated by the following examples wherein Example 1 shows the chemical modification of TentaGel® M $NH_2$ beads (grafted copolymers consisting of a low cross-linked polystyrene matrix on which a linear polyethylene glycol moiety is grafted) with a branched stable PEG reagent while Example 2 shows the chemical modification of TentaGel® M $NH_2$ beads with 40 kD or 60 kD branched stable PEG reagents; chemical modification of TentaGel® M $NH_2$ beads with polysialic acid is illustrated in Example 3; Example 4 describes coupling of branched PEG-SH to amino-functionalized beads via a Sulfo-EMCS spacer; Example 5 describes the coupling of a branched PEG-$NH_2$ to carboxyl functionalized beads by carbodiimide chemistry; Example 6 describes blood sample preparation and use of a the carrier of Example 1 in a method of the invention to detect anti-PEG antibody in the blood samples; Example 7 shows the detection method of Example 6 was specific for anti-PEG antibodies by a competition assay; Example 8 describes a comparison of the use of TentaGel beads in a method of the invention with the use of TentaGel beads modified with a branched PEG derivative; storage and stability tests of water soluble polymer-modified carriers according to the invention are described in Example 9; Example 10 describes an anti-PSA antibody detection assay of the invention; Example 11 reports the use of the anti-PEG antibody detection assay of Example 6 in preclinical studies in animal disease models and in untreated individuals; Example 12 describes coupling of PSH—SH to amino-functionalized beads via a Sulfo-EMCS spacer; Example 13 illustrates the coupling of PSA-$NH_2$ to polystyrene beads containing —OH groups; Example 14 describes the coupling of Hydroxy Ethyl Starch to TentaGel M $NH_2$ beads; and Example 15 shows the coupling of branched PSA to TentaGel M $NH_2$ beads.

Example 1

Chemical Modification of TentaGel® M $NH_2$ Beads with a Branched PEG Reagent (20 kD)

TentaGel® M $NH_2$ Beads (capacity: 0.24 mmol/g) were provided by Rapp Polymere (Tubingen, Germany) (grafted copolymers consisting of a low cross-linked polystyrene matrix on which a linear polyethylene glycol moiety is grafted). The primary amino group of the PEG chains of the beads was chemically modified with a branched PEGylation reagent (1,3-Bis(methoxypoly(ethylene glycol)carbamoyl)-2-propanoxy-4-succinimidyl butanoate) with a MW of 20 kD containing an active N-hydroxysuccinimide (NHS) group. 450 mg TentaGel® M $NH_2$ beads were suspended in 20 ml Buffer A (50 mM HEPES, 100 mM NaCl, pH 7.4). Then the suspension was centrifuged for 30 minutes (2800 RCF). The supernatant was discarded and the remaining beads were suspended again in 20 ml Buffer A. The suspension was gently shaken for five minutes and placed in an ultrasonic bath for 30 sec to avoid aggregates. Then the washing procedure was repeated and the pH of the suspension was controlled. Finally, the PEGylation reagent was dissolved in 2 mM HCl (75 mg/ml) and added to the beads suspension to give a concentration of 0.6 mg PEG reagent/mg TentaGel®. The PEGylation reaction was performed for 2 hours at room temperature with gentle shaking. Subsequently, the reaction was terminated by addition of a 0.1M glycine solution (final concentration: 0.01M). This solution was gently shaken again for 1 hour at room temperature. Then the PEGylated beads were centrifuged and reconstituted with Buffer B (20 mM HEPES, 150 mM NaCl, pH 7.4) as described above. This washing procedure was performed three times. Finally, the beads suspension was reconstituted in Buffer B, lyophilized and stored at 4° C.

Before using the beads, the beads were reconstituted in PBS and left for at least 1 hour to have time for swelling. The beads were washed with 20 ml PBS, centrifuged at 300 g for 5 minutes and the supernatant was discarded. This step was repeated and the pellet was reconstituted with an appropriate amount of PBS to get a 1% solution. Short sonication and filtration of the bead-solution should prevent any formation of clumps. The beads were counted and diluted if required to get a final concentration of about $2 \times 10^6$/ml.

Example 2

Chemical Modification of TentaGel® M $NH_2$ Beads with Branched PEG Reagents (40 kD and 60 kD)

The primary amino group of the PEG chains of TentaGel® M $NH_2$ beads (Rapp Polymere, Tübingen, Germany) (grafted copolymers consisting of a low cross-linked polystyrene matrix on which a linear polyethylene glycol moiety is grafted) was chemically modified with 40 kD or 60 kD branched PEGylation reagents (2,3-Bis(methylpolyoxyethylene-oxy)-1-(succinimidyl carboxypentyloxy)propane) containing an active NHSgroup. The reagents were obtained from NOF Corporation (Tokyo, Japan). Seventy-five mg TentaGel® M $NH_2$ beads were suspended in 20 ml Buffer A (50 mM HEPES, 100 mM NaCl, pH 7.4) and the suspension was gently shaken for five minutes and placed in an ultrasonic bath for 30 sec to avoid aggregates and gently shaken again for 5 minutes. Then the suspension was centrifuged for 30 minutes (2800 RCF). The supernatant was discarded and then the remaining beads were suspended again in 20 ml Buffer A and gently shaken for 10 minutes. Then the washing procedure was repeated and the pH of the suspension was controlled. Finally, the PEGylation reagents (Sunbright GL2-400GS2, MW 40 kD and Sunbright GL2-600GS2, MW 60 kD) were dissolved in 2 mM HCl (75 mg/ml) and added to the beads suspension to give a concentration of 0.75 mg PEG reagent/mg TentaGel®. The PEGylation reaction was performed for 2 hours at room temperature under gentle shaking.

Subsequently, the reaction was terminated by addition of a 0.1M Glycine solution (final concentration: 0.01M). This solution was gently shaken again for 1 hour at room temperature. Then the PEGylated beads were centrifuged and reconstituted with Buffer B (20 mM HEPES, 150 mM NaCl, pH 7.4) as described above. This washing procedure was performed three times. Finally the beads suspension was reconstituted in Buffer B, lyophilized and stored at 4° C.

Example 3

Chemical Modification of TentaGel® M $NH_2$ Beads with Polysialic Acid

Polysialic acid (Sigma) was purified by anion-exchange chromatography on Q-Sepharose FF (GE-Healthcare) and lyophilized. Then the PSA was oxidized with $NaIO_4$ [Fernandes and Gregoriadis, Biochim Biophys Acta, 1341: 26-34 (1997)], and a terminal aldehyde group was formed. Subsequently the PSA was coupled to TentaGel® M $NH_2$ beads (grafted copolymers consisting of a low cross-linked polystyrene matrix on which a linear polyethylene glycol moiety is grafted) by reductive amination with $NaCNBH_3$ as reductive agent.

Seventy-five mg TentaGel® M $NH_2$ beads (grafted copolymers consisting of a low cross-linked polystyrene matrix on which a linear polyethylene glycol moiety is grafted) were suspended in 10 ml Buffer A (50 mM HEPES, 350 mM NaCl, 5 mM $CaCl_2$, 0.01% Tween 80, pH 7.4) and the washing procedure was carried out as described in Example 2. Then PSA was added to give a final concentration of 85 mg/ml and the pH was adjusted to pH 7.4 by addition of 1 M NaOH. The coupling reaction was performed in Buffer A in the presence of $NaCNBH_3$ (3.17 mg/ml) in the cold room at 4° C. under gentle shaking for 16 hours. Finally the beads were centrifuged at 2800 RCF, resuspended in 10 ml Buffer B (20 mM HEPES, 150 mM NaCl, pH 7.4) and shaken for 10 minutes. The washing procedure was repeated two times. Finally the beads were resuspended in 2 ml Buffer B and lyophilized.

Example 4

Coupling of Branched PEG-SH to Amino-Functionalized Beads Via a Sulfo-EMCS Spacer Amino functionalized beads are obtained from Bangs Laboratories (Bangs Laboratories Inc., Fishers, Ind.) and washed with Buffer A as described in Example 2. Then Sulfo-EMCS (Pierce, Rockford, Ill.) is added to give a final concentration of 2 mg/ml and the reaction of the NHS ester of EMCS with the amino group of the beads is carried out for 2 hours at room temperature. Then the beads are centrifuged and washed 2 times as described in Example 2 and a branched PEG-SH with a molecular weight of 20 kD is added (final concentration 10 mg/ml). The coupling reaction of the free SH group to the MAL group of the spacer is performed at room temperature for 2 hours. Then the modified beads are centrifuged and washed 3 times as described in Example 2 and lyophilized.

Example 5

Coupling of a Branched PEG-$NH_2$ to Carboxyl Functionalized Beads by Carbodiimide Chemistry Carboxyl functionalized beads are obtained from Bangs Laboratories (Bangs Laboratories Inc., Fishers, Ind.) and coupled to a branched PEG-$NH_2$ with a M.W. of 40 kD (Sunbright GL-2 400PA), which is obtained from NOF (NOF Corporation, Tokyo, Japan). The coupling is performed by carbodiimide chemistry with water soluble EDAC (1-Ethyl-3[3-dimethylaminopropyl]carbodiimide). The coupling is carried out using a commercially available coupling kit obtained from Bangs Laboratories according to the instructions of the manufacturer.

Example 6

Blood Sample Preparation and Anti-PEG Antibody Detection Reaction

Blood samples taken from humans or animals were centrifuged for 10 minutes at 1100 g and once more for 20 minutes in order to isolate the plasma. Supernatant was collected and was ready for further use in the detection assay.

Twenty-five µl of the bead solution described in Example 1 together with 25 µl of the plasma samples were added to micronic tubes and vortexed. The mixture was incubated at room temperature for 30 minutes. The reaction was stopped by adding 1 ml PBS to the solution. It was then centrifuged at 200 g for 2 minutes and the supernatant was evacuated until 50 µl were left in the tube. This washing step was repeated once more.

To detect antibodies from the blood samples that were bound to the surface of the branched PEG-modified Tenta-Gel® beads, secondary antibodies labeled with fluorochromes were used. The secondary antibodies were diluted 1:32 with PBS and 5 µl of each antibody was added to the micronic tubes. The tubes were vortexed and incubated for 30 minutes at room temperature in the dark. The reaction was stopped again by adding 1 ml PBS to the solution. It was centrifuged at 200 g for 2 minutes and the supernatant was evacuated until 50 µl were left in the tube. This washing step was repeated once more and the pellet was reconstituted in 50 µl PBS. The samples were then analyzed by flow cytometry. FIG. 1 is a schematic diagram of the anti-PEG antibody detection assay Example 7

Competition Assay

To confirm the detection method of Example 6 was specific for anti-PEG antibodies a competition assay was established. A monoclonal rabbit IgG anti-PEG antibody was used as a positive control. The positive control was divided in two aliquots: one aliquot was pre-incubated with 5 µl of soluble PEG (wt 200) in different dilutions for 30 minutes at room temperature; the other aliquot was incubated with 5 µl PBS. The dilutions of the soluble PEG were done geometrically with PBS. As negative control, unstained beads and beads incubated with the secondary antibody were used.

Figure 2:
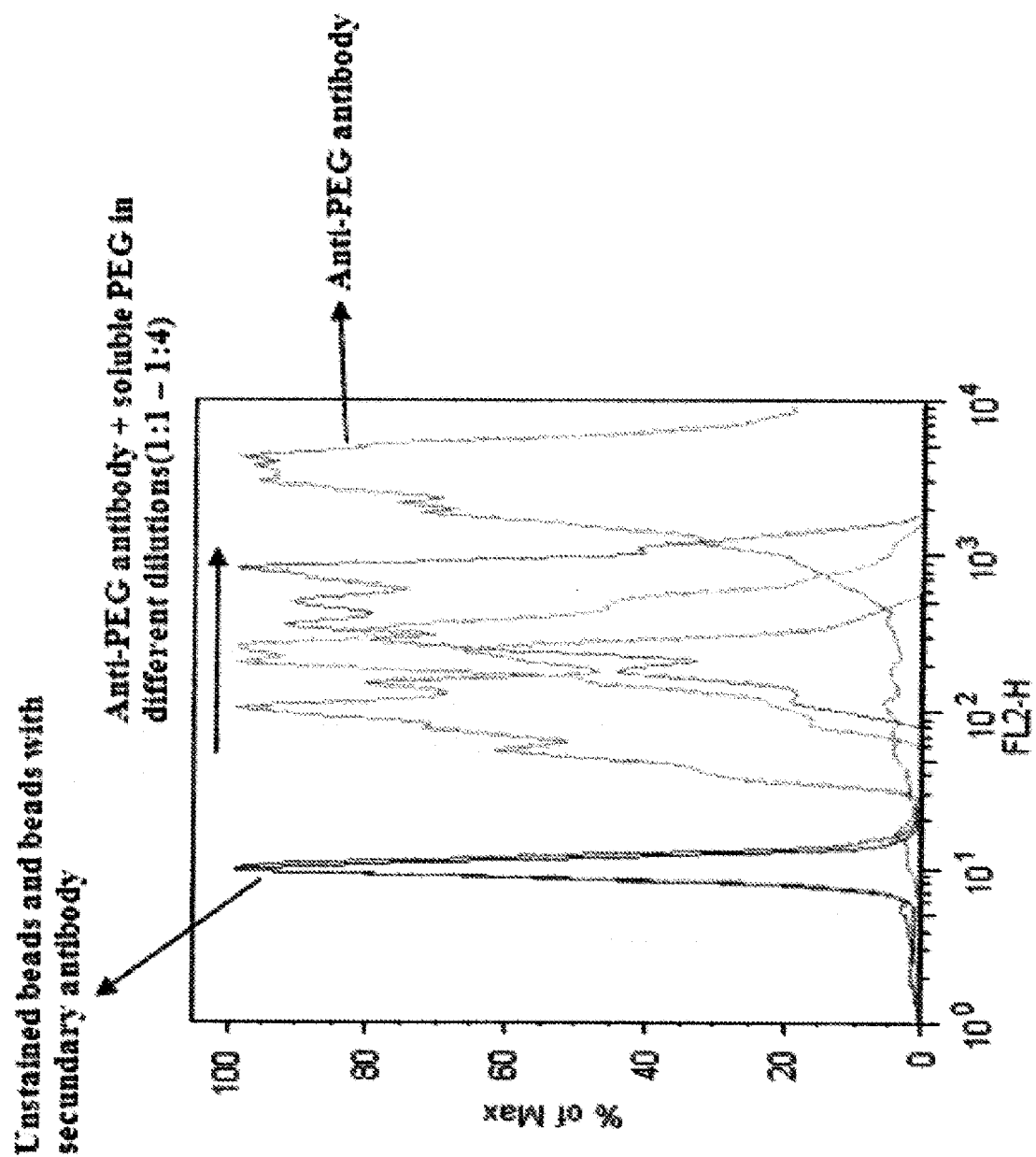

A reduction in median fluorescence intensity was observed after pre-incubation with the competitor and an increase again after diluting the competitor. Based on these results, seen in FIG. 2, the detected antibodies in the assay were specifically directed against PEG.

Example 8

Figure 3:
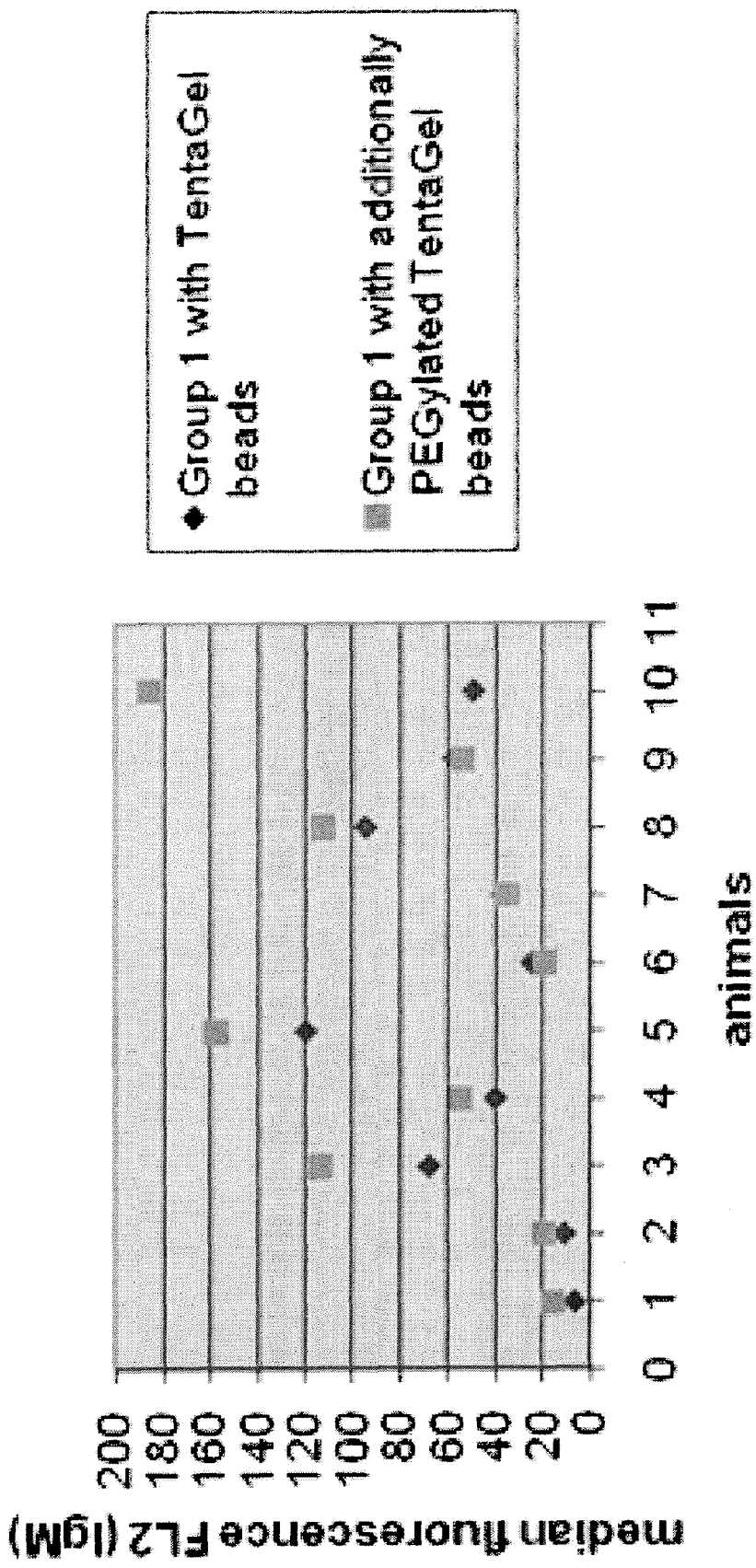
Figure 4:
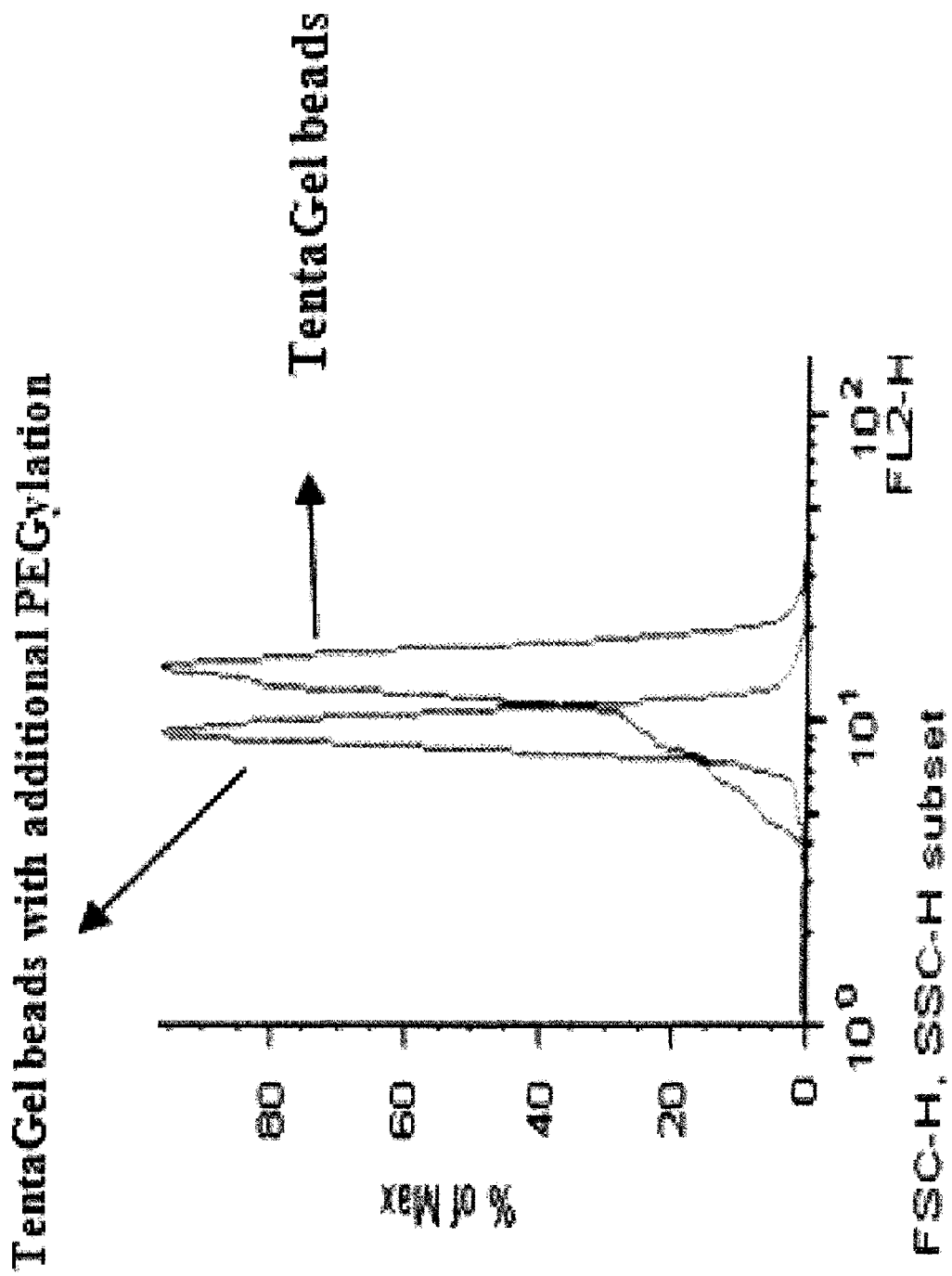

Use of TentaGel® Beads vs. TentaGel® Beads Modified with Branched PEG Derivative TentaGel® beads are grafted copolymers consisting of a low cross-linked polystyrene matrix on which a linear polyethylene glycol moiety is grafted. The copolymer contains about 50-70% PEG (w/w). Therefore, the properties of these polymers are highly dominated by the properties of PEG and no longer by the polystyrene matrix (Rapp Polymer GmbH). An experiment was conducted to determine whether additionally conjugating a branched chain PEG reagent to the TentaGel® beads provided improved identification of anti-PEG antibodies. To compare the conventional TentaGel® beads with the TentaGel® beads of Example 1 that were additionally PEGylated with a branched chain PEG derivative, the beads were used in the detection method of Example 6 to analyze plasma samples of mice treated intravenously with a PEGylated protein. Representative results are shown in FIG. 3 and indicate that the additional PEGylation with a branched chain PEG derivative improved the sensitivity of the assay. Moreover, beads coupled to branched PEG showed reduced auto fluorescence (FIG. 4) and were easier to handle because of a reduced tendency to aggregate.

Example 9

Storage and Stability Tests

Figure 5:
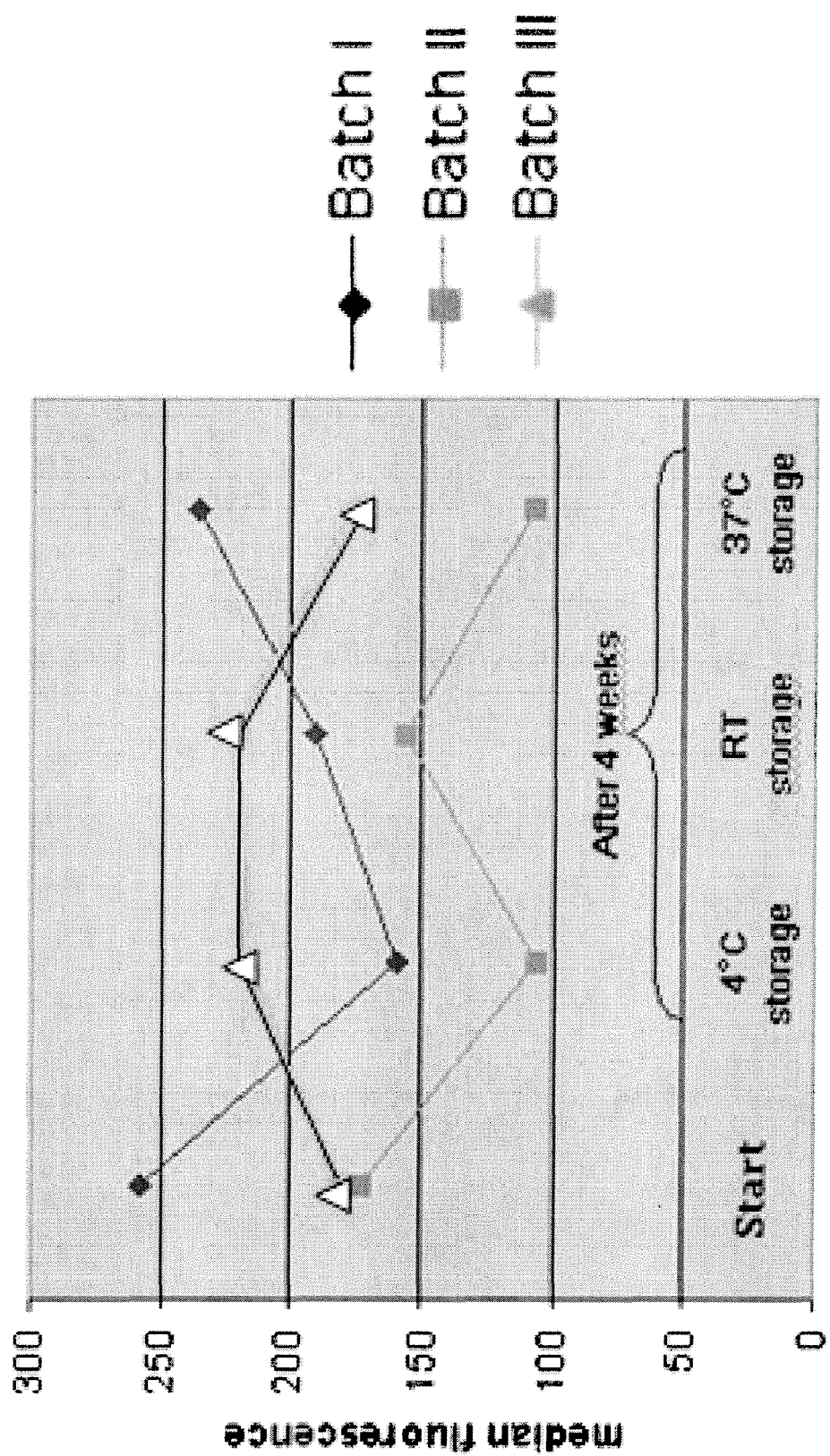

The modified beads of the Examples were lyophilized to guarantee their stability during storage. To explore the question of stability, three different batches of beads with additional PEGylation were produced according to Example 1 and lyophilized. Every lyophilized batch was stored under three different conditions, namely 4° C., room temperature and 37° C. The beads were tested with a protein A purified anti-PEG antibody from rabbit, before and after 4 weeks of storage. A murine monoclonal IgM anti-PEG antibody was used as positive control, unstained beads and beads incubated with secondary antibody only were used as negative control. FIG. 5 shows the beads exhibited no significant change in their median fluorescence intensity within a batch.

Example 10

Anti-PSA Antibody Detection Assay

Figure 6:
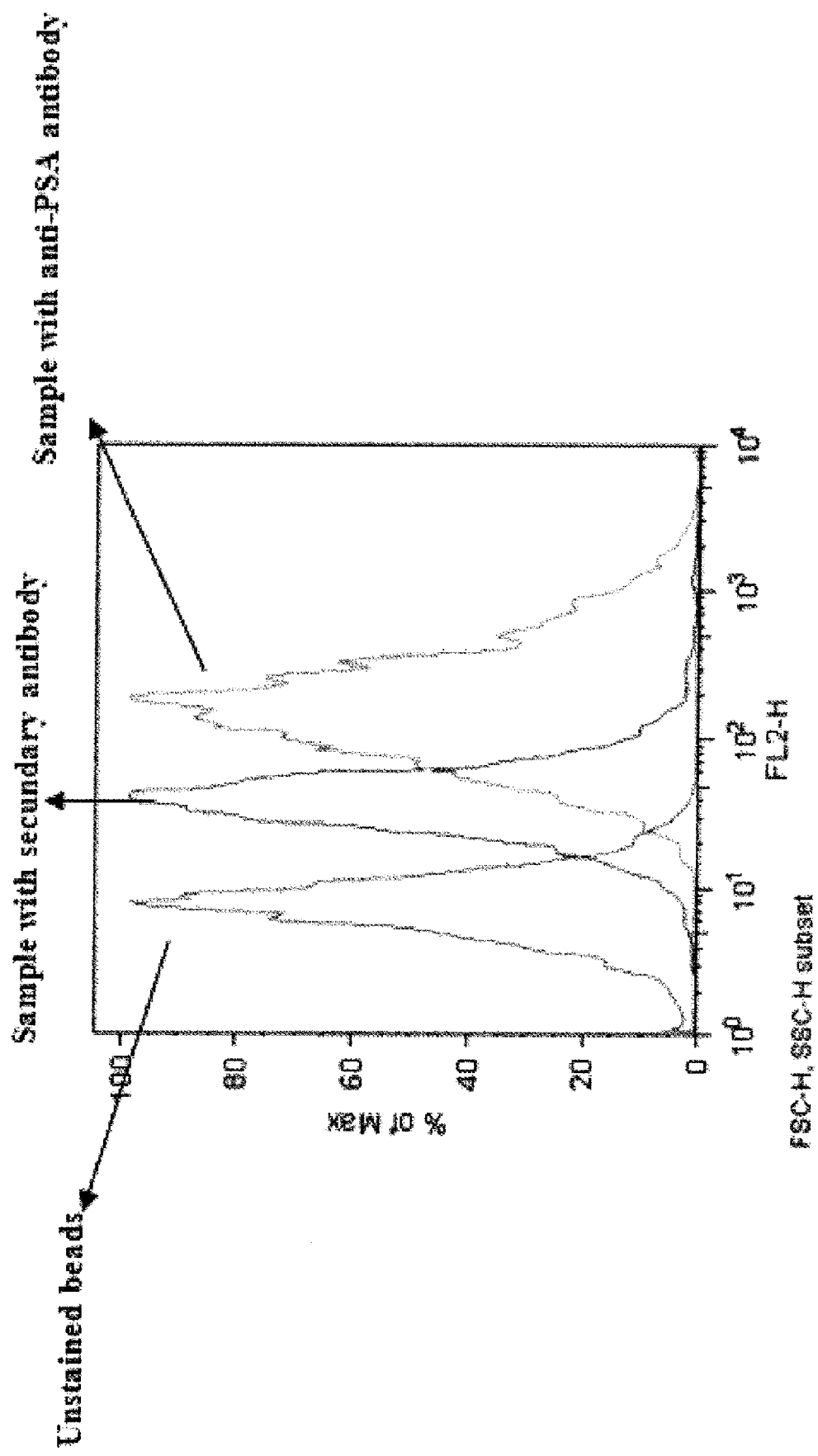
FIG. 6 shows the detection of a monoclonal anti-PSA antibody with PSA coupled beads in a flow cytometric approach.

The PSA-modified TentaGel® beads of Example 3 were used in the detection method of Example 6 (instead of the branched PEG-modified TentaGel® beads) to detect antibodies directed against PSA. The efficacy of the method was proven by using a monoclonal mouse anti-PSA antibody from Chemicon International as a positive control. As shown in FIG. 6, anti-PSA antibodies were detected.

Example 11

Practical Applications

The anti-PEG antibody detection assay of Example 6 was used in preclinical studies in animal disease models to monitoring the development of anti-PEG antibody. FIG. 7 shows the result of a study in which samples from rats immunized with PEG-Albumin were analyzed. The anti-PEG antibody titers were determined before (FIG. 7.1) and after (FIG. 7.2) immunization. Animals treated with PEG-Albumin developed antibodies against PEG.

The anti-PEG antibody detection assay of Example 6 was also used in preclinical studies to analyze blood samples from rats treated with PEG-Factor VIII. Anti-PEG antibody titers were determined before (FIG. 8.1) and after (FIG. 8.2) administration of the PEG-Factor VIII. Animals treated with PEG-Factor VIII developed antibodies against PEG.

Figure 9:
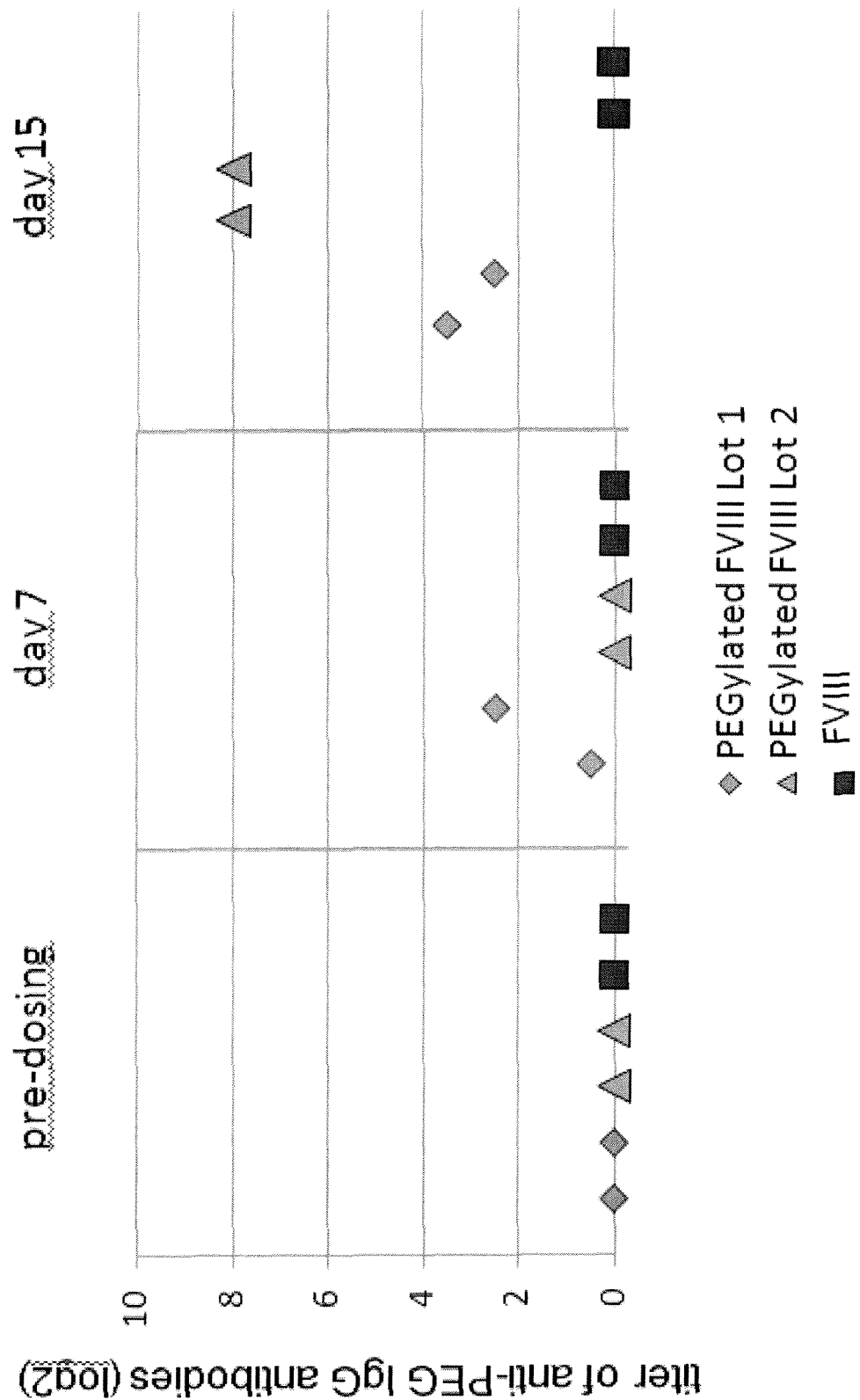
FIG. 9 shows evidence of anti-PEG antibodies in monkeys before treatment with PEGylated Factor VIII and after treatment in comparison with the protein without PEGylation.
Figure 10:
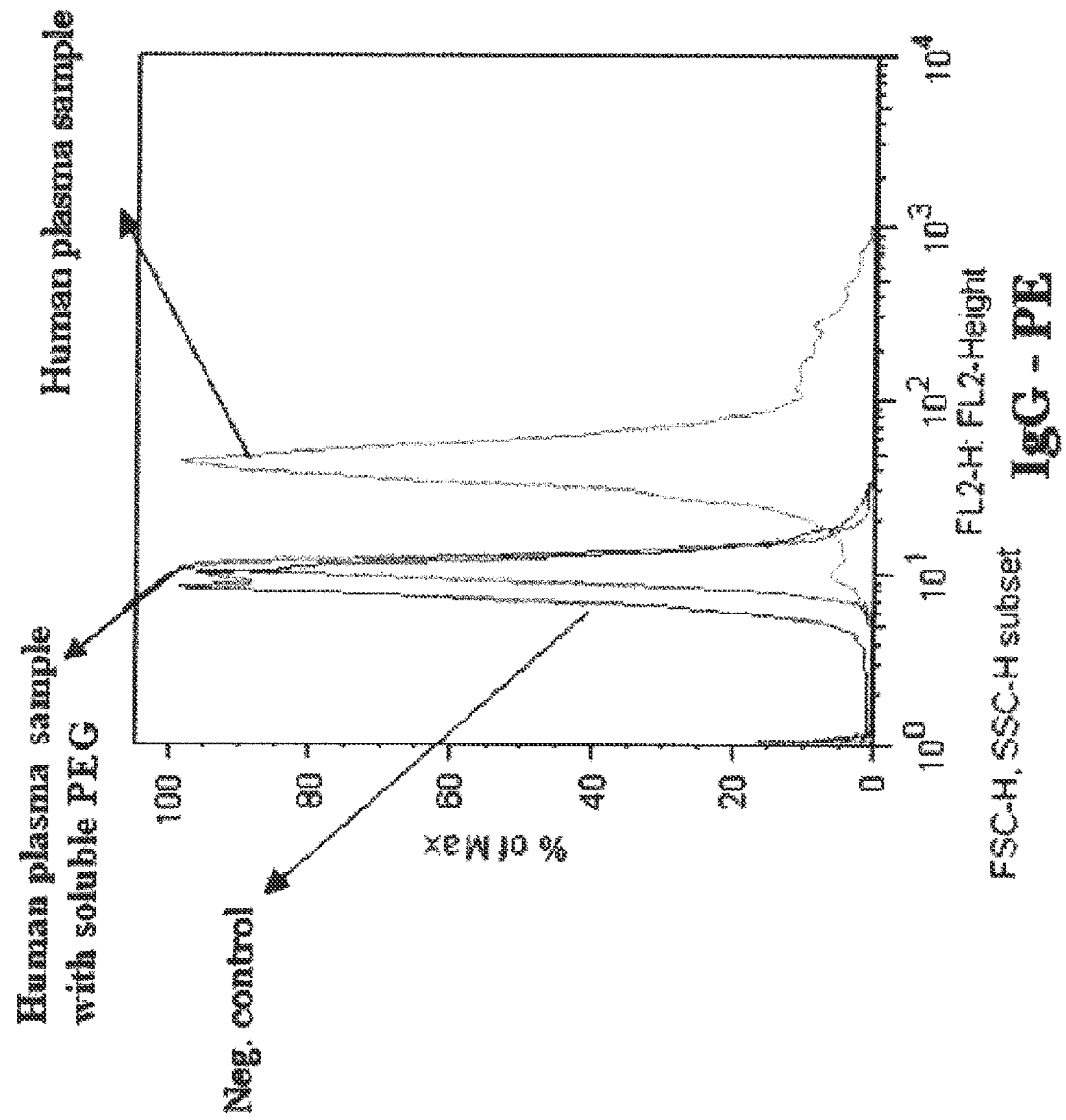
FIG. 10 shows a representative example of an IgG anti-PEG positive human plasma donor. The soluble PEG was given in a 10% concentration of total plasma volume.

The anti-PEG antibody detection assay of Example 6 was also used in preclinical studies to analyze blood samples from Cynomolgus monkeys treated with PEG-Factor VIII. FIG. 9 shows the result of a study where anti-PEG antibody titers were determined before and after administration of the PEG-Factor VIII. Animals treated with PEG-Factor VIII developed antibodies against PEG.

In addition, the assay of Example 6 was used to screen healthy human blood donors who have not been treated with a PEGylated drug for anti-PEG antibodies. To confirm that the detected antibodies are against PEG a competition assay was done. Each plasma sample was analyzed twice: one time with pre-incubation with the antigen and one time without. FIG. 8 shows a representative IgG anti-PEG antibody positive sample.

Example 12

Coupling of PSH—SH to Amino-Functionalized Beads Via a Sulfo-EMCS Spacer

Polysialic acid containing a terminal SH group (PSA-SH) was prepared as described in U.S. Pat. No. 7,683,158 B2. Polysialic acid was oxidized with $NaIO_4$ and a $NH_2$ group was formed by reductive amination with $NH_4Cl$ using $NaCNBH_3$ as reductive agent. Then, a terminal sulfhydryl group was introduced by reaction of the terminal $NH_2$ group with 2-iminothiolane (Traut's reagent/Pierce, Rockford, Ill.). Finally the PSA-SH preparation was purified by ultrafiltration/diafiltration using a 5 kD membrane made of regenerated cellulose (Millipore, Billerica, Mass.).

PSA-SH is coupled to beads as follows. Amino functionalized beads are obtained from Bangs Laboratories (Bangs Laboratories Inc., Fishers, Ind.) and washed with Buffer A as described in Example 1. Sulfo-EMCS (Pierce, Rockford, Ill.) is added to give a final concentration of 2 mg/ml and the reaction of the NHS ester of EMCS with the amino group of the beads is carried out for 2 hours at room temperature. Then the beads are centrifuged and washed 2 times as described in Example 2 and PSA-SH with a molecular weight of 20 kD is added (final concentration 10 mg/ml). The coupling reaction of the free SH group to the MAL group of the spacer is performed at room temperature for 2 hours. The modified beads are centrifuged and washed 3 times as described in Example 2 and lyophilized.

Example 13

Coupling of PS to Polystyrene Beads Containing —OH Groups

Polysialic acid containing a terminal $NH_2$ group (PSA-$NH_2$) was prepared as outlined in Example 12.

Polystyrene M-OH beads with a particle size of 10 μm were obtained from Rapp Polymeres (Tübingen, Germany). The beads are suspended in a $THF/H_2O$ mixture (4+1) and oxidized with the Dess-Martin Periodinane reagent [Hubbs and Heathrock, *J Am Chem Soc*, 125: 12836-12843 (2003) and Halligan and Nair, *ARKIVOC* (ii), 101-106 (2006)] for 3 hours at room temperature with gentle shaking. The beads containing free aldehyde groups are centrifuged and washed 3 times as described in Example 1. Then PSA-$NH_2$ is coupled to the beads by reductive amination as described in Example 3. A suspension of 75 mg oxidized beads containing free aldehyde groups is suspended in 10 ml Buffer A (50 mM HEPES, 350 mM NaCl, 5 mM $CaCl_2$, 0.01% Tween 80, pH 7.4). After washing PSA-$NH_2$ is added to give a final concentration of 85 mg/ml and the pH is adjusted to pH 7.4 by addition of 1 M NaOH. The coupling reaction is performed in Buffer A in the presence of NaCNBH$_3$ (3.17 mg/ml) in the cold room at 4° C. with gentle shaking for 16 hours. Finally the beads are centrifuged at 2800 RCF, resuspended in 10 ml Buffer B (20 mM HEPES, 150 mM NaCl, pH 7.4) and shaken for 10 minutes. The washing procedure is repeated two times. Finally the beads are resuspended in 2 ml Buffer B and lyophilized.

Example 14

Coupling of Hydroxy Ethyl Starch to TentaGel® M NH$_2$ Beads

Hydroxyethyl starch (HES) is coupled to TentaGel® M NH$_2$ beads (Rapp Polymere, Tübingen, Germany) (grafted copolymers consisting of a low cross-linked polystyrene matrix on which a linear polyethylene glycol moiety is grafted) containing free NH$_2$ groups. An example of hydroxyethyl starch is HES from potatoes, which is commercially available from Serumwerke Bernburg (Bernburg, Germany). HES with a molecular weight of 70 kD is oxidized with Cu$^{2+}$ ions and converted into the lactone form as described in U.S. Pat. No. 7,541,328 B2. A suspension of seventy-five mg TentaGel® M NH$_2$ Beads in 10 ml Buffer A (50 mM HEPES, 350 mM NaCl, 5 mM CaCl$_2$, 0.01% Tween 80, pH 7.4) is prepared and the washing procedure is carried out as described in Example 1. Then the HES derivative (lactone form) is added to give a final concentration of 25 mg/ml and the pH is adjusted to pH 7.4 by addition of 1 M NaOH. The coupling reaction is performed in Buffer A in the presence of NaCNBH$_3$ (1.5 mg/ml) in the cold room at 4° C. with gentle shaking for 16 hours. Subsequently the beads are centrifuged at 2800 RCF, resuspended in 10 ml Buffer B (20 mM HEPES, 150 mM NaCl, pH 7.4) and shaken for 10 minutes. The washing procedure is repeated two times. Finally the beads are resuspended in 2 ml Buffer B and lyophilized.

Example 15

Coupling of Branched PSA to TentaGel® M NH$_2$ Beads

A branched PSA reagent is prepared by use of the multifunctional cross-linking reagent Succinimidyl-3,5-dimaleimidophenyl benzoate (SDMB) [Schott et al., *Bioconjugate Chem*, 4: 153-165 (1993)], which is commercially available (Molecular Biosciences, Boulder, Colo.). The procedure is performed in two steps.

First, SDMB is coupled to TentaGel® M NH$_2$ beads (grafted copolymers consisting of a low cross-linked polystyrene matrix on which a linear polyethylene glycol moiety is grafted). SDMB is solved in DMF (10 mg/ml) and added in a 10 fold excess to a suspension of TentaGel® M NH$_2$ Beads (5 mg/ml) in Buffer A (50 mM HEPES, 100 mM NaCl, pH 7.4) to give 5 mg beads per ml buffer. The coupling of SDMB to the amino groups of the beads is carried out via the N-hydroxysuccinimide (NHS) group by forming a stable amide bond. The reaction is carried out for 2 hours at room temperature with gentle shaking. Then, the suspension is centrifuged for 30 min (2800 RCF). The supernatant is discarded and the remaining beads are suspended again in 20 ml Buffer A. Then the washing procedure is repeated two times and the pH of the suspension is controlled.

Second, PSA-SH is coupled to the SDMB-derivatized beads. PSA-SH is prepared as outlined in Example 12 and is coupled to the maleimide (MAL) groups of the SDMB linker. PSA-SH is added in a 25 fold excess to the beads suspension and the coupling reaction is carried out for 2 hours at room temperature. Then free MAL residues are blocked by the addition of cysteine (50 fold excess). Finally, the beads are centrifuged at 2800 RCF and resuspended in Buffer B (50 mM Hepes, 150 mM NaCl, pH 7.4). This washing procedure is repeated two times.

The present invention is illustrated by the foregoing examples and variations thereof will be apparent to those skilled in the art. Therefore, no limitations other than those set out in the following claims should be placed on the invention.

We claim:

1. A method of detecting an antibody to a polyethylene glycol (PEG)-modified polypeptide in a sample suspected of containing the antibody to the PEG-modified polypeptide, the method comprising the steps of:
   a) contacting the sample with a water soluble polymer-modified carrier and
   b) detecting binding of the antibody to the water soluble polymer on the water soluble polymer-modified carrier,
   wherein the water soluble polymer-modified carrier comprises water soluble polymer-modified beads, wherein the water soluble polymer is a non-linear PEG polymer, and wherein binding is indicative of the presence of the antibody to the PEG-modified polypeptide.

2. The method of claim 1 wherein the polypeptide is a blood coagulation protein.

3. The method of claim 1 or 2 wherein the non-linear PEG polymer has a glycerol backbone with 1, 2 or 1,3 substitution pattern or has a lysine backbone.

4. The method of claim 1 or 2 wherein the non-linear PEG polymer is 1,3-Bis(methoxypoly(ethylene glycol)carbamoyl)-2-propanoxy-4-succinimidyl butanoate.

5. The method of claim 1 or 2 wherein the non-linear PEG polymer is linked directly to the carrier via an amide bond.

6. The method of claim 1 or 2 wherein the non-linear PEG polymer is linked directly to the carrier via an amine group.

7. The method of claim 1 or 2 wherein the non-linear PEG polymer is linked to the carriers via a spacer molecule.

8. The method of claim 7 wherein the spacer molecule is DSS (Disuccinimidyl suberate), BS3 (Bis[Sulfosuccinimidyl]suberate), EMCS(N-[ε-Maleimidocaproyloxy]succinimide ester), sulfo-EMCS(N-[ε-Maleimidocaproyloxy]sulfosuccinimide ester, MBS (m-Maleimidobenzoyl-N-hydroxysuccinimide ester), sulfo-MBS (m-Maleimidobenzoyl-N-hydroxysulfosuccinimide ester), sulfo-KMUS (N-[κ-Maleimidoundecanoyloxy]-sulfosuccinimide ester) or KMUA (N-κ-Maleimidoundecanoic acid).

9. The method of claim 1 or 2 wherein the water soluble polymer-modified beads are polystyrene beads, silica beads, latex beads or poly(methyl methacrylate) (PMMA) beads modified with a water soluble polymer.

10. The method of claim 9 wherein the water soluble polymer-modified polystyrene beads are polystyrene beads with linear PEG attached via an ethyl ether group, and wherein the non-linear PEG polymer is linked to the linear PEG via an amide bond.

11. The method of claim 2 wherein the water soluble polymer-modified blood coagulation protein is PEGylated Factor VIII.

12. The method of claim 2 wherein the water soluble polymer-modified blood coagulation protein is PEGylated Factor IX.

13. The method of claim 2 wherein the water soluble polymer-modified blood coagulation protein is PEGylated Factor VIIa.

* * * * *